(12) United States Patent
Harada et al.

(10) Patent No.: US 9,439,725 B2
(45) Date of Patent: Sep. 13, 2016

(54) ABLATION CATHETER WITH BALLOON (75) Inventors: Hiroyuki Harada, Otsu (JP); Motoki Takaoka, Otsu (JP); Akinori Matsukuma, Otsu (JP); Takahiro Yagi, Otsu (JP)

(73) Assignee: Toray Industries, Inc. (JP)

( * ) Notice: Subject to any disclaimer, the term of this patent is extended or adjusted under 35 U.S.C. 154(b) by 208 days.

(21) Appl. No.: 14/123,595

(22) PCT Filed: Jun. 8, 2012

(86) PCT No.: PCT/JP2012/064752
§ 371 (c)(1),
(2), (4) Date: Dec. 3, 2013

(87) PCT Pub. No.: WO2012/169607
PCT Pub. Date: Dec. 13, 2012

(65) Prior Publication Data
US 2014/0114306 A1    Apr. 24, 2014

(30) Foreign Application Priority Data

Jun. 8, 2011 (JP) ................................. 2011-128052

(51) Int. Cl.
*A61B 18/12* (2006.01)
*A61B 18/14* (2006.01)
*A61B 18/00* (2006.01)

(52) U.S. Cl.
CPC .... *A61B 18/1492* (2013.01); *A61B 2018/0022* (2013.01); *A61B 2018/00357* (2013.01);
(Continued)

(58) Field of Classification Search
CPC ................... A61B 18/1492; A61B 2018/022; A61B 2018/00357; A61B 2018/00434; A61B 2018/00511; A61B 2018/00577; A61B 2018/00642; A61B 2018/00702; A61B 2018/00821
See application file for complete search history.

(56) References Cited

U.S. PATENT DOCUMENTS 5,344,398 A * 9/1994 Hara ........................... 604/97.01
5,486,173 A * 1/1996 Vancaillie ............ A61B 18/149
606/45

(Continued)

FOREIGN PATENT DOCUMENTS

JP    2002-078809 A    3/2002
JP    2003-111848 A    4/2003

(Continued)

*Primary Examiner* — Michael Peffley
*Assistant Examiner* — Daniel Fowler
(74) *Attorney, Agent, or Firm* — DLA Piper LLP (US)

(57) ABSTRACT

A balloon ablation catheter achieves reduction in diameter of the balloon upon balloon contraction and increased reliability of the thermocouple temperature sensor, which balloon ablation catheter is less likely to be influenced by the heating liquid discharged into the balloon and able to control the balloon surface temperature with high accuracy. The balloon ablation catheter includes a shaft wherein a lumen is formed; a balloon wherein the lumen communicates with the inside thereof; and a high-frequency-current-applying electrode formed by coiling a high-frequency-power-supplying lead wire around the shaft while sandwiching a temperature sensor lead wire between the high-frequency-power-supplying lead wire and the shaft such that the temperature sensor lead wire is fixed along the longitudinal direction of the shaft; wherein a thermocouple thermosensor is formed at the point where the high-frequency-power-supplying lead wire and the temperature sensor lead wire constituting the high-frequency-current-applying electrode contact with each other for the first time as seen from the posterior end side in the longitudinal direction.

4 Claims, 5 Drawing Sheets (52) U.S. Cl.
CPC ............... *A61B2018/00434* (2013.01); *A61B 2018/00511* (2013.01); *A61B 2018/00577* (2013.01); *A61B 2018/00642* (2013.01); *A61B 2018/00702* (2013.01); *A61B 2018/00821* (2013.01)

(56) References Cited

U.S. PATENT DOCUMENTS

| | | | |
|---|---|---|---|
| 6,258,087 B1 * | 7/2001 | Edwards et al. | 606/41 |
| 2002/0004644 A1 * | 1/2002 | Koblish | 604/104 |
| 2002/0029062 A1 | 3/2002 | Satake | |
| 2002/0087156 A1 | 7/2002 | Maguire et al. | |
| 2005/0203597 A1 | 9/2005 | Yamazaki et al. | |
| 2007/0149963 A1 | 6/2007 | Matsukuma et al. | |
| 2008/0172050 A1 | 7/2008 | Satake | |
| 2010/0069836 A1 * | 3/2010 | Satake | 604/96.01 |

FOREIGN PATENT DOCUMENTS

| | | |
|---|---|---|
| JP | 4062935 B2 | 1/2008 |
| JP | 4222152 B2 | 11/2008 |
| JP | 4226040 B2 | 12/2008 |

* cited by examiner

ABLATION CATHETER WITH BALLOON

TECHNICAL FIELD

This disclosure relates to a balloon ablation catheter.

BACKGROUND

Catheter ablation is a method to treat arrhythmia by inserting an ablation catheter into the heart chamber and cauterizing the cardiac muscle tissue with an electrode attached to the anterior end of the catheter.

A recently developed balloon ablation catheter is used by percutaneously introducing a balloon attached to the anterior end side of the catheter into the inferior vena cava and then delivering it via the right atrium and then the interatrial septum of the heart to the left atrium, where the balloon is inflated and heated with high-frequency power to cauterize the cardiac muscle tissue (JP 2002-78809 A and JP 4062935 B). This catheter has now become the mainstream in catheter ablation.

In the use of a balloon ablation catheter, a balloon attached to the anterior end of the catheter is inflated with a heating liquid, and a high-frequency current is applied between a counter electrode plate outside the body of the patient and a high-frequency-current-applying electrode arranged inside the balloon, to heat the heating liquid. The whole cardiac muscle tissue that is in contact with the balloon surface is thus cauterized. The temperature of the balloon surface is controlled by a temperature sensor arranged inside the balloon, and the heating liquid inside the balloon is made uniform by stirring with an oscillator or the like.

A thermocouple temperature sensor in which a metal wire that supplies high-frequency power to the high-frequency-current-applying electrode is point-bonded to a different type of metal wire is often used as the temperature sensor for the balloon ablation catheter. It is said that in such a case, arrangement of the thermocouple near the posterior end of, and on the surface of, the high-frequency-current-applying electrode allows secure positioning of the thermocouple inside the balloon, leading to increased reliability of the detected temperature (JP 4226040 B). However, at the same time, since the thermocouple temperature sensor is positioned near the lumen that communicates with the inside of the balloon, the sensor is likely to be directly influenced by cooling with the heating liquid discharged for stirring into the balloon so that there is a problem of instability of control of the balloon surface temperature.

On the other hand, to suppress the influence of cooling with the heating liquid discharged into the balloon, an attempt has been made to arrange the thermocouple temperature sensor in the anterior end portion of the high-frequency-current-applying electrode (JP 4222152 B).

However, if the thermocouple temperature sensor is arranged in the anterior end side of the high-frequency-current-applying electrode, the different type of metal wire needs to be further extended to the anterior end side in the balloon. In this case, the flexibility of the catheter in the portion where the different type of metal wire is extended is deteriorated, and the balloon diameter upon contraction near the high-frequency-current-applying electrode increases, resulting in difficulty in introducing the balloon ablation catheter into the body of the patient and disadvantages in terms of operation of the catheter and the burden on the patient.

Further, wherever the thermocouple temperature sensor is arranged on the surface of the high-frequency-current-applying electrode, point bonding of the different type of metal wire needs secure adhesion by soldering or the like, and this adhesion is one of the factors that increase the balloon diameter upon balloon contraction. Further, since the strength of the thermocouple prepared by point bonding of the different type of metal wire cannot be fully reliable, development of measures to suppress the risk of wire breakage and the like is an urgent task, and improvement of reliability of the thermocouple temperature sensor has been demanded.

It could therefore be helpful to provide a balloon ablation catheter that achieves reduction in the diameter of the balloon upon balloon contraction and increased reliability of the thermocouple temperature sensor, which balloon ablation catheter is less likely to be influenced by the heating liquid discharged into the balloon and able to control the balloon surface temperature with high accuracy.

SUMMARY

We thus provide (1) to (4) below:
(1) A balloon ablation catheter comprising: a shaft in which a lumen penetrates in the longitudinal direction; a balloon fixed to the shaft, wherein the lumen communicates with the inside of the balloon; and a high-frequency-current-applying electrode arranged inside the balloon, which electrode is formed by coiling, around the shaft, a high-frequency-power-supplying lead wire that supplies high-frequency power from power supply means, while sandwiching, between the high-frequency-power-supplying lead wire and the shaft, a temperature sensor lead wire that supplies a measured signal to the power supply means such that the temperature sensor lead wire is fixed along the longitudinal direction of the shaft; wherein a thermocouple thermosensor is formed at the point where the high-frequency-power-supplying lead wire and the temperature sensor lead wire constituting the high-frequency-current-applying electrode contact with each other for the first time as seen from the posterior end side in the longitudinal direction.
(2) The balloon ablation catheter according to (1), comprising an oscillator that gives oscillation to a heating liquid in the balloon by repeating suction and discharge of the heating liquid from the lumen.
(3) The balloon ablation catheter according to (1) or (2), wherein the thermocouple temperature sensor is formed at the posterior end portion of the high-frequency-current-applying electrode.
(4) The balloon ablation catheter according to any one of (1) to (3), wherein the temperature sensor lead wire reaches the anterior end portion of the high-frequency-current-applying electrode.

With the balloon ablation catheter, the diameter of the balloon upon balloon contraction can be further reduced, and the burden on the patient upon introduction of the balloon ablation catheter into the body can be reduced. Further, the thermocouple temperature sensor of the balloon ablation catheter is less likely to be influenced by the heating liquid discharged into the balloon, and has a low risk of wire breakage and the like so that the balloon surface temperature can be controlled with high accuracy.

DESCRIPTION OF SYMBOLS

1, Balloon ablation catheter (Example)
2, Balloon
3, High-frequency-current-applying electrode
4a, 4b, 4c, Thermocouple temperature sensor
5, Outer cylindrical shaft
6, Inner cylinder shaft
7, High-frequency power generator connector
8, High-frequency-power-supplying lead wire
9, Temperature sensor lead wire
12, Luer lock
13, Y-shaped connector
14, Artificial pulmonary vein
15, Thermocouple for measuring the balloon surface temperature
16, Counter electrode plate
17, High-frequency power generator
18, Guide wire
19, Thermocouple data logger

DETAILED DESCRIPTION

Preferred examples are described below in detail with reference to the drawings, but this disclosure is not limited to these examples. Each identical factor is represented using an identical symbol, and redundant explanations are omitted. The ratios used in the drawings are not necessarily the same as those in the description.

Our balloon ablation catheters are characterized in that they comprise: a shaft in which a lumen penetrates in the longitudinal direction; a balloon fixed to the shaft, wherein the lumen communicates with the inside of the balloon; and a high-frequency-current-applying electrode arranged inside the balloon, which electrode is formed by coiling, around the shaft, a high-frequency-power-supplying lead wire that supplies high-frequency power from power supply means, while sandwiching, between the high-frequency-power-supplying lead wire and the shaft, a temperature sensor lead wire that supplies a measured signal to the power supply means such that the temperature sensor lead wire is fixed along the longitudinal direction of the shaft; and that a thermocouple thermosensor is formed at the point where the high-frequency-power-supplying lead wire and the temperature sensor lead wire constituting the high-frequency-current-applying electrode contact with each other for the first time as seen from the posterior end side in the longitudinal direction.

Figure 1:
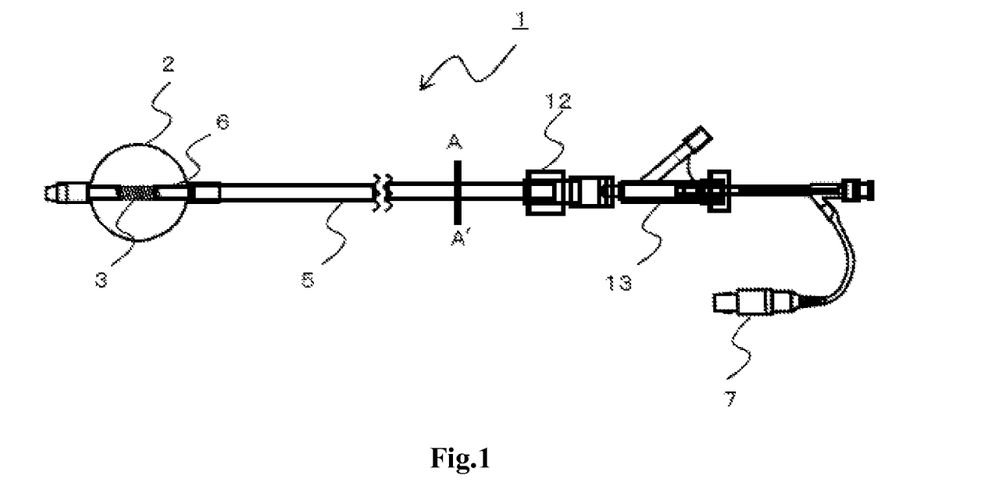
FIG. 1 is a schematic diagram illustrating the balloon ablation catheter of a first example.
Figure 2:
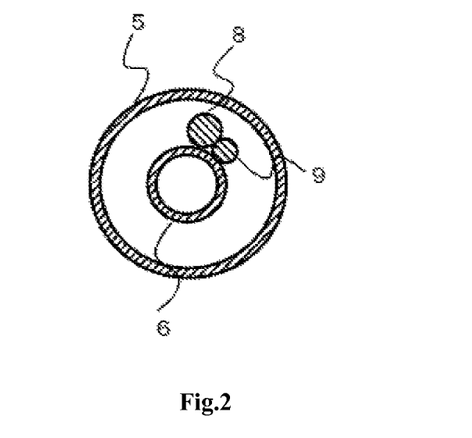
FIG. 2 is a schematic diagram illustrating the cross section along the A-A' line in the shaft portion of the balloon ablation catheter of the first example.

FIG. 1 is a schematic diagram illustrating the balloon ablation catheter of a first example. FIG. 2 is a schematic diagram illustrating the cross section along the A-A' line in the shaft portion of the balloon ablation catheter of the first example.

The balloon ablation catheter 1 illustrated in FIG. 1 comprises: a balloon 2 in the anterior end side, which can be inflated and contracted; a high-frequency-current-applying electrode 3 and a thermocouple temperature sensor in the balloon 2; a double cylindrical shaft composed of an inner cylinder shaft 6 inserted in the lumen of an outer cylindrical shaft 5; and a high-frequency power generator connector 7 in the posterior end side. Further, the space between the outer cylindrical shaft 5 and the inner cylinder shaft 6 illustrated in FIG. 2, that is, lumen, communicates with the inside of the balloon 2, and a high-frequency-power-supplying lead wire 8 and a temperature sensor lead wire 9 are inserted through this space.

The shape of the balloon 2 is not limited as long as the balloon fits the blood vessel. For example, a spherical shape having a diameter of 20 to 40 mm is preferred. The wall thickness of the balloon 2 is preferably 20 to 120 µm, more preferably 20 to 50 µm.

The material of the balloon 2 is preferably an elastic material excellent in antithrombogenicity, more preferably a polyurethane polymer material. Examples of the polyurethane polymer material include thermoplastic polyether urethane, polyether polyurethane urea, fluorine polyether urethane urea, polyether polyurethane urea resin and polyether polyurethane urea amide.

The "shaft in which a lumen penetrates in the longitudinal direction" is preferably a double cylindrical shaft comprising an inner cylinder shaft 6 inserted in the lumen of an outer cylindrical shaft 5, as shown in FIG. 1.

The method to fix the balloon 2 to the outer cylindrical shaft 5 or the inner cylinder shaft 6 is preferably welding. As shown in FIG. 1, in cases where the anterior end portion of the balloon 2 is fixed to the anterior end portion in the longitudinal direction of the inner cylinder shaft 6 and the posterior end portion of the balloon 2 is fixed to the anterior end portion in the longitudinal direction of the outer cylindrical shaft 5, the longitudinal length of the balloon 2 can be changed by sliding between the inner cylinder shaft 6 and the outer cylindrical shaft 5, which is preferred. Alternatively, both ends of the balloon 2 may be fixed to only one of the inner cylinder shaft 6 and the outer cylindrical shaft 5.

The length of each of the outer cylindrical shaft 5 and the inner cylinder shaft 6 is preferably 500 to 1700 mm, more preferably 600 to 1200 mm. The material of each of the outer cylindrical shaft 5 and the inner cylinder shaft 6 is preferably a flexible material excellent in antithrombogenicity, and examples of the material include fluorocarbon resins, polyamide resins, polyurethane resins and polyimide resins. The outer cylindrical shaft 5 preferably has an outer diameter of 3.0 to 4.0 mm, and an inner diameter of 2.5 to 3.5 mm. The inner cylinder shaft 6 preferably has an outer diameter of 1.5 to 1.7 mm, and an inner diameter of 1.2 to 1.3 mm. The outer cylindrical shaft 5 may have a multilayer structure.

Figure 3:
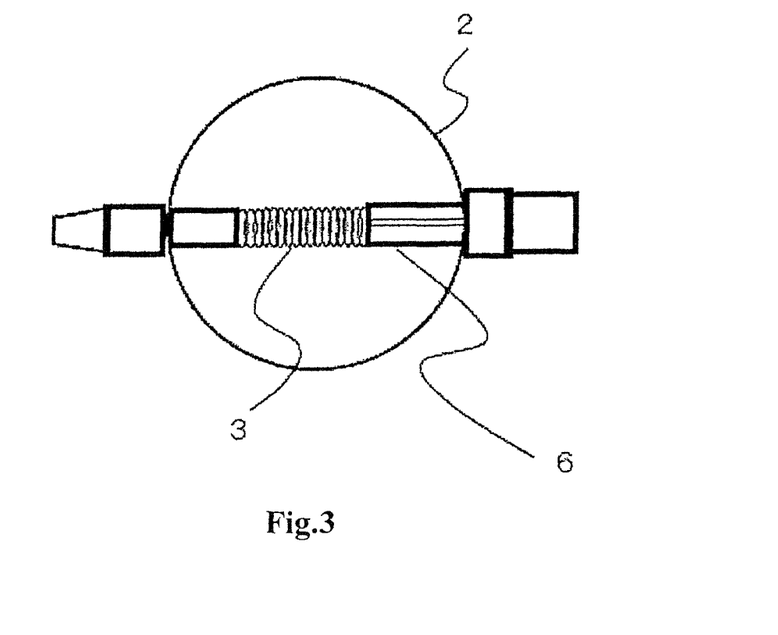
FIG. 3 is a schematic diagram illustrating the outer appearance in the vicinity of the anterior end of the balloon ablation catheter of the first example.
Figure 4:
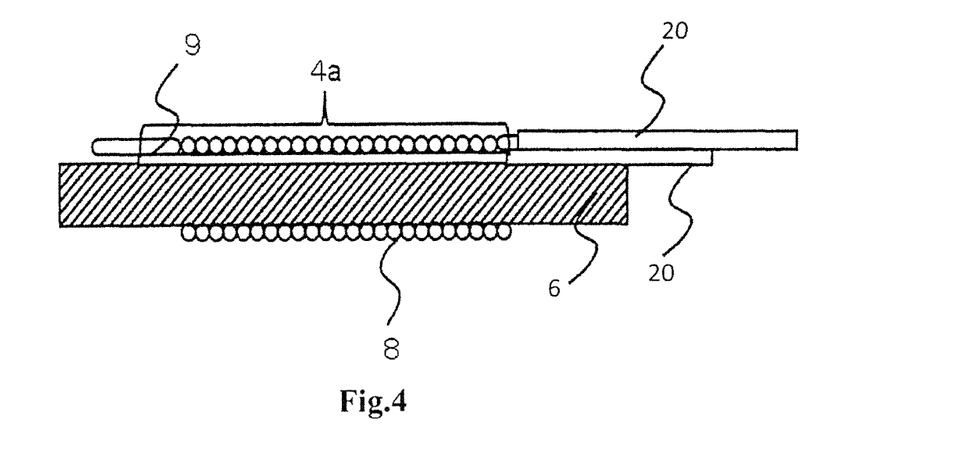
FIG. 4 is a schematic diagram illustrating a cross section horizontal to the longitudinal direction near the high-frequency-current-applying electrode of the balloon ablation catheter of the first example.

FIG. 3 is a schematic diagram illustrating the outer appearance in the vicinity of the anterior end of the balloon ablation catheter of the first example. FIG. 4 is a schematic diagram illustrating a cross section horizontal to the longitudinal direction near the high-frequency-current-applying electrode of the balloon ablation catheter of the first example.

The high-frequency-current-applying electrode 3 is arranged in the balloon 2, and, in cases where the "shaft in which a lumen penetrates in the longitudinal direction" is a double cylindrical shaft as shown in FIG. 1, the high-frequency-current-applying electrode 3 is preferably formed by coiling the high-frequency-power-supplying lead wire 8 around the inner cylinder shaft 6 as shown in FIG. 4. The high-frequency-power-supplying lead wire 8 forming the high-frequency-current-applying electrode 3 has a diameter of preferably 0.1 to 1 mm, more preferably 0.2 to 0.5 mm. Examples of the material of the high-frequency-power-supplying lead wire 8 include highly conductive metals such as copper, silver, gold, platinum, tungsten and alloys, and it is preferred to prevent short circuit, to apply an electrically insulating protective coating 19 with a fluorocarbon resin or the like to the wire except for the portion where the high-frequency-current-applying electrode 3 is formed.

The thermocouple temperature sensor 4a is a thermocouple temperature sensor formed at the point where the high-frequency-power-supplying lead wire 8 and the temperature sensor lead wire 9 contact each other for the first time as seen from the posterior end side in the longitudinal direction, when the electrode is formed by coiling the high-frequency-power-supplying lead wire 8 around the inner cylinder shaft 6 while sandwiching the temperature sensor lead wire 9 between the high-frequency-power-supplying lead wire 8 and the inner cylinder shaft 6.

Since the thermocouple temperature sensor 4a is formed while the temperature sensor lead wire 9 is sandwiched between the high-frequency-power-supplying lead wire 8 and the inner cylinder shaft 6, the thermocouple temperature sensor 4a is consequently arranged between the high-frequency-current-applying electrode 3 and the inner cylinder shaft 6, that is, on the inner surface of the high-frequency-current-applying electrode 3.

The balloon ablation catheter preferably comprises an oscillator that gives oscillation to the heating liquid in the balloon by repeating suction and discharge of the heating liquid from the lumen that communicates with the inside of the balloon.

Examples of the oscillator that gives oscillation to the heating liquid in the balloon include devices comprising a roller pump, diaphragm pump, bellows pump, vane pump, centrifugal pump, or a pump comprising a combination of a piston and a cylinder.

Since, in a high-frequency-current-applying electrode, high-frequency power is most likely to be concentrated at the ends of the electrode, the thermocouple temperature sensor of the balloon ablation catheter is preferably formed at an end portion of the high-frequency-current-applying electrode, preferably formed at the posterior end portion of the high-frequency-current-applying electrode.

In cases where the balloon ablation catheter 1 has the oscillator and, in addition, the thermocouple temperature sensor 4a is formed at the posterior end portion of the high-frequency-current-applying electrode 3 as illustrated in FIG. 4, the thermocouple temperature sensor 4a is consequently positioned near the lumen that communicates with the inside of the balloon 2. However, since the thermocouple temperature sensor 4a is arranged on the inner surface of the high-frequency-current-applying electrode 3 rather than on the outer surface of the high-frequency-current-applying electrode 3, the thermocouple temperature sensor 4a is less likely to be influenced by cooling with the heating liquid discharged for stirring into the balloon 2, while being largely influenced by conduction of heat from the high-frequency-current-applying electrode 3. As a result, stable high-frequency power is supplied to the high-frequency-current-applying electrode 3 so that the surface temperature of the balloon 2 can be remarkably stabilized.

Since the thermocouple temperature sensor 4a is fixed by coiling the high-frequency-power-supplying lead wire 8 around the inner cylinder shaft 6 while sandwiching the temperature sensor lead wire 9 between the high-frequency-power-supplying lead wire 8 and the inner cylinder shaft 6 such that the temperature sensor lead wire 9 is fixed along the longitudinal direction of the inner cylinder shaft 6, the thermocouple temperature sensor 4a does not need to be attached by soldering or the like at all, unlike the thermocouple of the prior art. As a result, the balloon diameter upon contraction of the balloon 2 can be reduced so that the balloon ablation catheter 1 can be easily introduced into the body of the patient.

The thermocouple temperature sensor 4a is fixed by coiling the high-frequency-power-supplying lead wire 8 around the inner cylinder shaft 6 while sandwiching the temperature sensor lead wire 9 between the high-frequency-power-supplying lead wire 8 and the inner cylinder shaft 6 such that the temperature sensor lead wire 9 is fixed along the longitudinal direction of the inner cylinder shaft 6. Therefore, the temperature sensor lead wire 9 is inserted between the inner cylinder shaft 6 and the high-frequency-power-supplying lead wire 8, and extends to the anterior end side in the longitudinal direction as seen from the position of the thermocouple temperature sensor 4a. The temperature sensor lead wire 9 is preferably in contact at a plurality of points with the high-frequency-power-supplying lead wire 8 forming the high-frequency-current-applying electrode 3. Further, as illustrated in FIG. 4, the temperature sensor lead wire 9 is more preferably in contact with the high-frequency-power-supplying lead wire 8 along the entire length of the high-frequency-current-applying electrode. That is, the temperature sensor lead wire 9 more preferably reaches the anterior end portion of the high-frequency-current-applying electrode 3.

Being inserted between the inner cylinder shaft 6 and the high-frequency-power-supplying lead wire 8, the temperature sensor lead wire 9 is fixed on the inner cylinder shaft 6 by the high-frequency-power-supplying lead wire 8. Therefore, fixation of the thermocouple temperature sensor 4a to the balloon ablation catheter 1 in this case is stronger than in a case where soldering or the like is carried out. As a result, the strength as a thermocouple temperature sensor remarkably increases, and the risk of wire breakage, loose connection and the like can be suppressed so that the reliability remarkably increases.

Further, since the temperature sensor lead wire 9 is compactly housed in the small space between the inner cylinder shaft 6 and the high-frequency-power-supplying lead wire 8, deflection or the like of the temperature sensor lead wire 9 never occurs. As a result, as compared to cases where the temperature sensor lead wire 9 is extended into the space in the balloon 2, the balloon diameter upon contraction of the balloon 2 can be reduced, and the flexibility of the catheter is not deteriorated.

The diameter of the temperature sensor lead wire 9 is preferably 0.1 to 0.6 mm, more preferably 0.1 to 0.3 mm. Examples of the material of the temperature sensor lead wire 9 include constantan and, to prevent short circuit, an electrically insulating protective coating 20 with a fluorocarbon resin or the like is preferably applied to the portion posterior to the position where the temperature sensor 4a is formed.

The posterior end of each of the high-frequency-power-supplying lead wire 8 and the temperature sensor lead wire 9 inserted through the space between the outer cylindrical shaft 5 and the inner cylinder shaft 6 shown in FIG. 2 is further inserted through a Y-shaped connector 13, and connected to the high-frequency power generator connector 7.

The material of the Y-shaped connector 13 is preferably an electrically insulating material such as a polycarbonate or ABS resin.

The high-frequency power generator connector 7 comprises a highly conductive metal pin therein. Examples of the material of the highly conductive metal pin include copper, silver, gold, platinum, tungsten and alloys. The surface of the highly conductive metal pin is protected with an electrically insulating and chemically resistant material. Examples of the material include polysulfone, polyurethane, polypropylene and polyvinyl chloride.

EXAMPLES

A specific example of the balloon ablation catheter is described below with reference to drawings. The term "length" herein means the length in the longitudinal direction.

Example

While a polyurethane tube was drawn, air was injected into the lumen of the tube to perform blow molding. By this, a polyurethane balloon 2 having a diameter of 30 mm and a thickness of 20 μm was prepared.

A polyurethane tube having an outer diameter of 4 mm, inner diameter of 3 mm and a total length of 1000 mm was used as the outer cylindrical shaft 5. A Y-shaped connector 13 was inserted and fitted in a luer lock 12 provided at an end of the tube, and fixed by bonding. A polyimide tube having an outer diameter of 1.8 mm, inner diameter of 1.4 mm and a total length of 1100 mm was used as the inner cylinder shaft 6.

A copper wire having a diameter of 0.3 mm with an electrically insulating protective coating was used as the high-frequency-power-supplying lead wire 8, and a constantan wire having a diameter of 0.1 mm with an electrically insulating protective coating was used as the temperature sensor lead wire 9.

A part of the electrically insulating protective coating applied to each of the high-frequency-power-supplying lead wire 8 and the temperature sensor lead wire 9 was removed and, from the position 20 mm away from the anterior end of the inner cylinder shaft 6, the high-frequency-power-supplying lead wire 8 was coiled around the inner cylinder shaft 6 while the temperature sensor lead wire 9 was sandwiched between the high-frequency-power-supplying lead wire 8 and the inner cylinder shaft 6, to form a coil-shaped high-frequency-current-applying electrode 3 having a length of 13 mm and a thermocouple temperature sensor 4a arranged at the posterior end portion of the high-frequency-current-applying electrode 3.

The anterior end and the posterior end of the formed high-frequency-current-applying electrode 3 were fixed to the inner cylinder shaft 6 by welding with a polyurethane tube.

The inner cylinder shaft 6 was inserted into the outer cylindrical shaft 5. The anterior end portion of the balloon 2 was fixed by welding at the position 10 mm away from the anterior end of the inner cylinder shaft 6, and the posterior end portion of the balloon 2 was fixed by welding at the anterior end portion of the outer cylindrical shaft 5.

The high-frequency-power-supplying lead wire 8 and the temperature sensor lead wire 9 were inserted through the space between the outer cylindrical shaft 5 and the inner cylinder shaft 6, and through the Y-shaped connector 13. The posterior end of each wire was connected to a high-frequency power generator connector 7, to complete the balloon ablation catheter (hereinafter referred to as the "Example catheter").

Comparative Example 1

Figure 5:
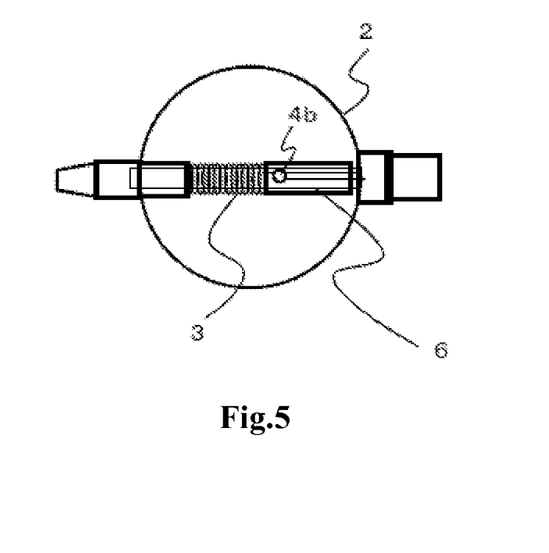
FIG. 5 is a schematic diagram illustrating the outer appearance in the vicinity of the anterior end of the balloon ablation catheter of Comparative Example 1.
Figure 6:
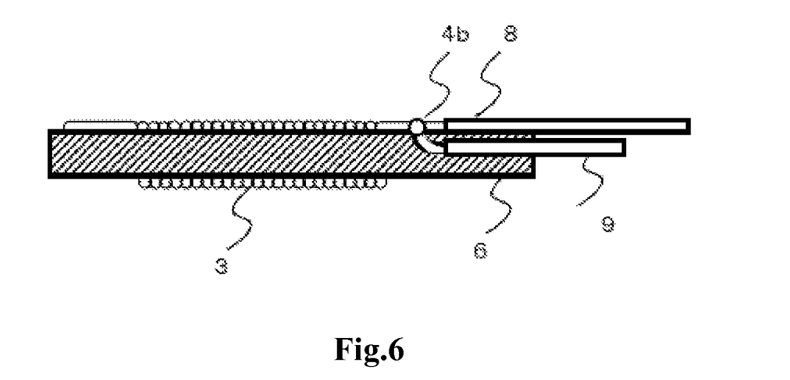
FIG. 6 is a schematic diagram illustrating a cross section horizontal to the longitudinal direction near the high-frequency-current-applying electrode of the balloon ablation catheter of Comparative Example 1.

A balloon ablation catheter (hereinafter referred to as the "Comparative Example 1 catheter") was completed in the same manner as in Example except for the method of forming the high-frequency-current-applying electrode and the thermocouple temperature sensor. FIG. 5 is a schematic diagram illustrating the outer appearance in the vicinity of the anterior end of the Comparative Example 1 catheter. FIG. 6 is a schematic diagram illustrating a cross section horizontal to the longitudinal direction near the high-frequency-current-applying electrode of the Comparative Example 1 catheter.

The high-frequency-current-applying electrode 3 and the thermocouple temperature sensor 4b of the Comparative Example 1 catheter were formed as follows. First, a part of the electrically insulating protective coating applied to each of the high-frequency-power-supplying lead wire 8 and the temperature sensor lead wire 9 was removed and, from the position 20 mm away from the anterior end of the inner cylinder shaft 6, the high-frequency-power-supplying lead wire 8 was coiled around the inner cylinder shaft 6 to form a coil-shaped high-frequency-current-applying electrode 3 having a length of 10 mm. Thereafter, the anterior end of a constantan wire 9 having a diameter of 0.1 mm was point-bonded by soldering on the surface of the high-frequency-power-supplying lead wire 8 at the position 2 mm away from the posterior end of the high-frequency-current-applying electrode 3 to form a thermocouple temperature sensor 4b. The anterior end and the posterior end of the formed high-frequency-current-applying electrode 3 were fixed to the inner cylinder shaft 6 using a heat-shrinkable tube.

Comparative Example 2

Figure 7:
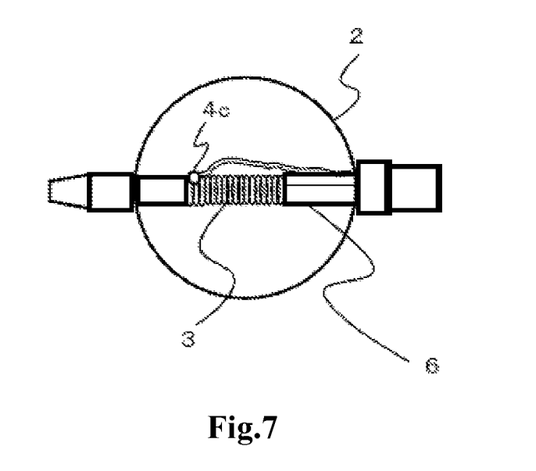
FIG. 7 is a schematic diagram illustrating the outer appearance in the vicinity of the anterior end of the balloon ablation catheter of Comparative Example 2.
Figure 8:
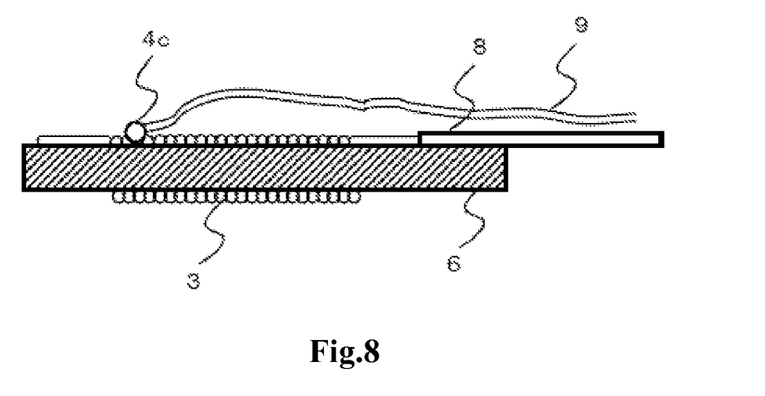
FIG. 8 is a schematic diagram illustrating a cross section horizontal to the longitudinal direction near the high-frequency-current-applying electrode of the balloon ablation catheter of Comparative Example 2.

A balloon ablation catheter (hereinafter referred to as the "Comparative Example 2 catheter") was completed in the same manner as in Example except for the method of forming the high-frequency-current-applying electrode and the thermocouple temperature sensor. FIG. 7 is a schematic diagram illustrating the outer appearance in the vicinity of the anterior end of the Comparative Example 2 catheter. FIG. 8 is a schematic diagram illustrating a cross section horizontal to the longitudinal direction near the high-frequency-current-applying electrode of the Comparative Example 2 catheter.

The high-frequency-current-applying electrode 3 and the thermocouple temperature sensor 4c of the Comparative Example 2 catheter were formed as follows. First, a part of the electrically insulating protective coating applied to each of the high-frequency-power-supplying lead wire 8 and the temperature sensor lead wire 9 was removed and, from the position 20 mm away from the anterior end of the inner cylinder shaft 6, the high-frequency-power-supplying lead wire 8 was coiled around the inner cylinder shaft 6 to form a coil-shaped high-frequency-current-applying electrode 3 having a length of 12 mm. Thereafter, the anterior end of a constantan wire 9 having a diameter of 0.1 mm was point-bonded by soldering on the surface of the anterior end of the high-frequency-current-applying electrode 3, to form a thermocouple temperature sensor 4c. The anterior end and the posterior end of the high-frequency-current-applying electrode 3 were fixed to the inner cylinder shaft 6 using a heat-shrinkable tube.

Measurement of Balloon Surface Temperature

Figure 9:
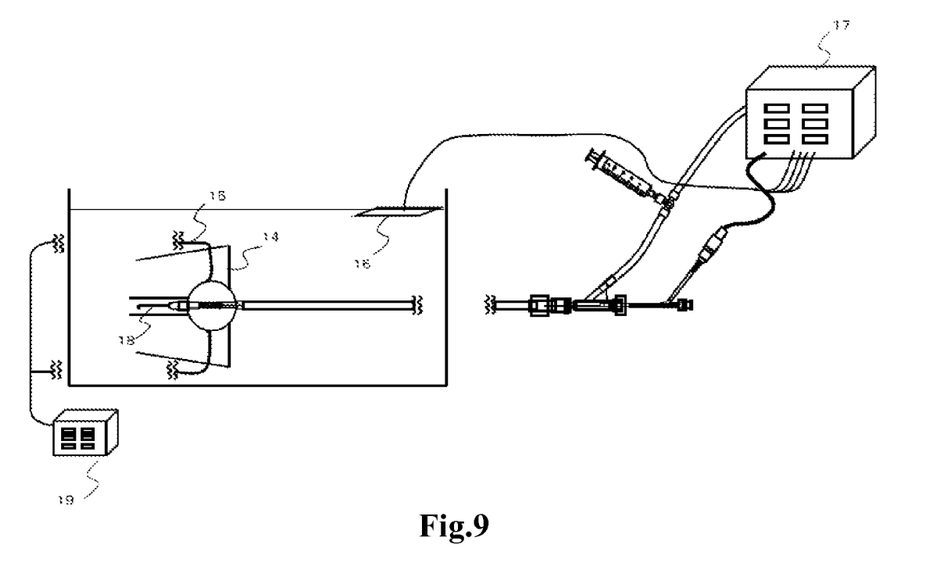
FIG. 9 is a schematic diagram illustrating an assay system for measurement of the balloon surface temperature of a balloon ablation catheter.

FIG. 9 is a schematic diagram showing an evaluation system for measuring the balloon surface temperature of the balloon ablation catheter.

The balloon 2 of the Example catheter was expanded with a dilute contrast medium (2-fold diluted with physiological saline) to a balloon diameter of 28 mm. By sliding between the inner cylinder shaft 6 and the outer cylindrical shaft 5, the length of the balloon 2 (hereinafter referred to as the "balloon length") was adjusted to 30 mm.

The balloon 2 was soaked in a tank filled with physiological saline, and the balloon 2 was inserted into a pulmonary vein 14 artificially prepared using an acrylic polymer material. A thermocouple 15 for measurement of the balloon surface temperature was placed in contact with the upper and lower surfaces of the balloon 2.

A counter electrode plate 16 for applying a high-frequency current was soaked in a tank, and the high-frequency power generator connector 7 and the counter electrode plate 16 of the Example catheter were connected to a high-frequency power generator 17. Through the inner cylinder shaft 6 of the Example catheter, a guide wire 18 was inserted.

A high-frequency power (frequency, 1.8 MHz; maximum power, 150 W; preset temperature, 70° C.) was applied to the catheter. The balloon surface temperature during the application of power was recorded by a thermocouple data logger 19, and the high-frequency output and the temperature in the balloon measured by the thermocouple temperature sensor 4a were recorded in the high-frequency power generator 17.

In the same manner as described above except that the balloon length was 25 mm (this makes the thermocouple temperature sensor 4a more likely to be influenced by cooling by the heating liquid discharged into the balloon), the balloon surface temperature during the application of high-frequency power was recorded.

The Comparative Example 1 catheter and the Comparative Example 2 catheter were also tested in the same manner as described above for the cases of a balloon length of 30 mm and a balloon length of 25 mm, and the balloon surface temperature during the application of high-frequency power was recorded.

The maximum temperature on the balloon surface during the application of high-frequency power observed for each of the Example catheter, Comparative Example 1 catheter and Comparative Example 2 catheter is shown in Table 1. In the Example catheter and the Comparative Example 2 catheter, the maximum temperature on the balloon surface was hardly influenced by the change in the balloon length. However, only in the Comparative Example 1 catheter, the maximum temperature of the balloon surface in the case of a balloon length of 25 mm was 66.1° C., which was about 4° C. higher than that in the case of a balloon length of 30 mm. Moreover, this maximum temperature was higher than 65° C., which is a heating temperature that may cause pulmonary vein stenosis.

TABLE 1

|  | Balloon length | |
| --- | --- | --- |
|  | 30 mm | 25 mm |
| Example catheter | 61.9° C. | 62.7° C. |
| Comparative Example 1 catheter | 62.2° C. | 66.1° C. |
| Comparative Example 2 catheter | 63.1° C. | 63.7° C. |

Measurement of Maximum Diameter of Balloon

The maximum diameter of the balloon 2 upon contraction was measured for each of the Example catheter, Comparative Example 1 catheter and Comparative Example 2 catheter. As a result, the maximum diameter of the balloon 2 was 2.38 mm in the Example catheter, 2.68 mm in the Comparative Example 1 catheter, and 2.64 mm in the Comparative Example 2 catheter. Thus, a reduction in the diameter of about 0.3 mm was achieved with the Example catheter as compared to the Comparative Example 1 catheter and the Comparative Example 2 catheter.

INDUSTRIAL APPLICABILITY

Our catheters can be used as balloon ablation catheters for treatment of arrhythmia such as atrial fibrillation, endometriosis, cancer cells, hypertension, and the like in the medical field.

The invention claimed is:

1. A balloon ablation catheter comprising:
    an outer shaft in which a lumen penetrates in a longitudinal direction;
    an inner shaft in which a lumen penetrates in a longitudinal direction and inserted in the lumen of the outer shaft,
    a balloon fixed to said outer shaft, wherein said lumen of the outer shaft communicates with an inside portion of the balloon;
    a high-frequency-current-applying electrode arranged inside said balloon, which electrode is formed by coiling-a high-frequency-power-supplying lead wire that supplies high-frequency power from a power supply around said inner shaft; and
    a temperature sensor lead wire that supplies a measured signal to the power supply sandwiched and fixed between the coiled high-frequency-power-supplying lead wire and the inner shaft along the longitudinal direction of the inner shaft; and
    a thermocouple formed in the balloon and at a point where said high-frequency-power-supplying lead wire and said temperature sensor lead wire contact each other for the first time as seen from a posterior end side in the longitudinal direction;
    wherein the temperature sensor lead wire is fixed on the inner shaft by the coiled high-frequency-power-supplying lead wire and is inserted between the coiled high-frequency-power-supplying lead wire and the inner shaft, and said temperature sensor lead wire is in contact at a plurality of points with said coiled high-frequency-power-supplying lead wire and said shaft in the balloon.

2. The balloon ablation catheter according to claim 1, comprising an oscillator that oscillates a heating liquid in said balloon by repeating suction and discharge of the heating liquid from said lumen.

3. The balloon ablation catheter according to claim 1, wherein said temperature sensor lead wire reaches an anterior end portion of said high-frequency-current-applying electrode.

4. The balloon ablation catheter according to claim 1, wherein said temperature sensor lead wire and said high-frequency-power-supplying lead are formed from different metals.

* * * * *